US00PP20704P2

(12) United States Plant Patent
Dofferhoff

(10) Patent No.: US PP20,704 P2
(45) Date of Patent: Feb. 2, 2010

(54) ***GENTIANA* PLANT NAMED 'BLUE MAGIC'**
(50) Latin Name: *Gentiana makinoi*
Varietal Denomination: Blue Magic

(76) Inventor: Hans Dofferhoff, Middelburgseweg 1, Reeuwijk 2811 PL (NL)

( * ) Notice: Subject to any disclaimer, the term of this patent is extended or adjusted under 35 U.S.C. 154(b) by 0 days.

(21) Appl. No.: 12/291,663

(22) Filed: Nov. 12, 2008

(51) Int. Cl.
*A01H 5/00* (2006.01)

(52) U.S. Cl. ..... Plt./433
(58) Field of Classification Search ..... Plt./433
See application file for complete search history.

*Primary Examiner*—Annette H Para
(74) *Attorney, Agent, or Firm*—Penny J. Aguirre

(57) ABSTRACT

A new cultivar of *Gentiana makinoi* named 'Blue Magic', characterized by its numerous light blue flowers borne on well-branched stems, its compact plant habit, and its early flowering season in mid early to mid summer.

2 Drawing Sheets

Botanical classification: *Gentiana makinoi.*
Varietal denomination: 'Blue Magic'.

BACKGROUND OF THE INVENTION

The present invention relates to a new and distinct cultivar of *Gentiana makinoi* and will be referred to hereafter by its cultivar name, 'Blue Magic'. 'Blue Magic' represents a new Gentian, an herbaceous perennial grown for landscape use.

The inventor discovered the new cultivar, 'Magic Purple', as a chance seedling that arose in a cultivated trial garden in his nursery in Reeuwijk, The Netherlands in the summer of 2006. Although the parentage is unknown, *Gentiana makinoi* 'Marsha' (U.S. Plant Pat. No. 16,562) and an unnamed plant of *Gentiana scabra* are likely parents based on the characteristics of 'Blue Magic' and their proximity in the same growing area.

Asexual reproduction of the new cultivar was first accomplished by in vitro propagation under the direction of the inventor in Rijswijk, The Netherlands in 2007. It has been determined that the characteristics of the new cultivar are stable and are reproduced true to type in successive generations.

SUMMARY OF THE INVENTION

The following traits have been repeatedly observed and represent the characteristics of the new cultivar after observing plants grown outdoors in a field for two years in Reeuwijk, The Netherlands. These attributes in combination distinguish 'Blue Magic' from all other varieties of Gentians known to the inventor.

1. 'Blue Magic' exhibits flowers that are light blue in color.
2. 'Blue Magic' exhibits a dwarf and compact plant habit.
3. 'Blue Magic' exhibits well-branched stems and numerous flowers.
4. 'Blue Magic' is early flowering with flowers present in June and July in The Netherlands.

'Blue Magic' differs from its likely parent plant, 'Marsha' in having a greater number of lateral branches, in having flowers that are lighter blue in color and in having an earlier flowering season. 'Blue Magic' differs from its likely parent, *Gentiana scabra,* in being taller in height, in having smaller flowers, and in having an earlier flowering season.

BRIEF DESCRIPTION OF THE PHOTOGRAPHS

The plants and plant parts in the photographs were taken of cut stems of 'Blue Magic' that were harvested from two-year old plants that were grown outdoors in a field plot in Reeuwijk, The Netherlands.

Figure 1:
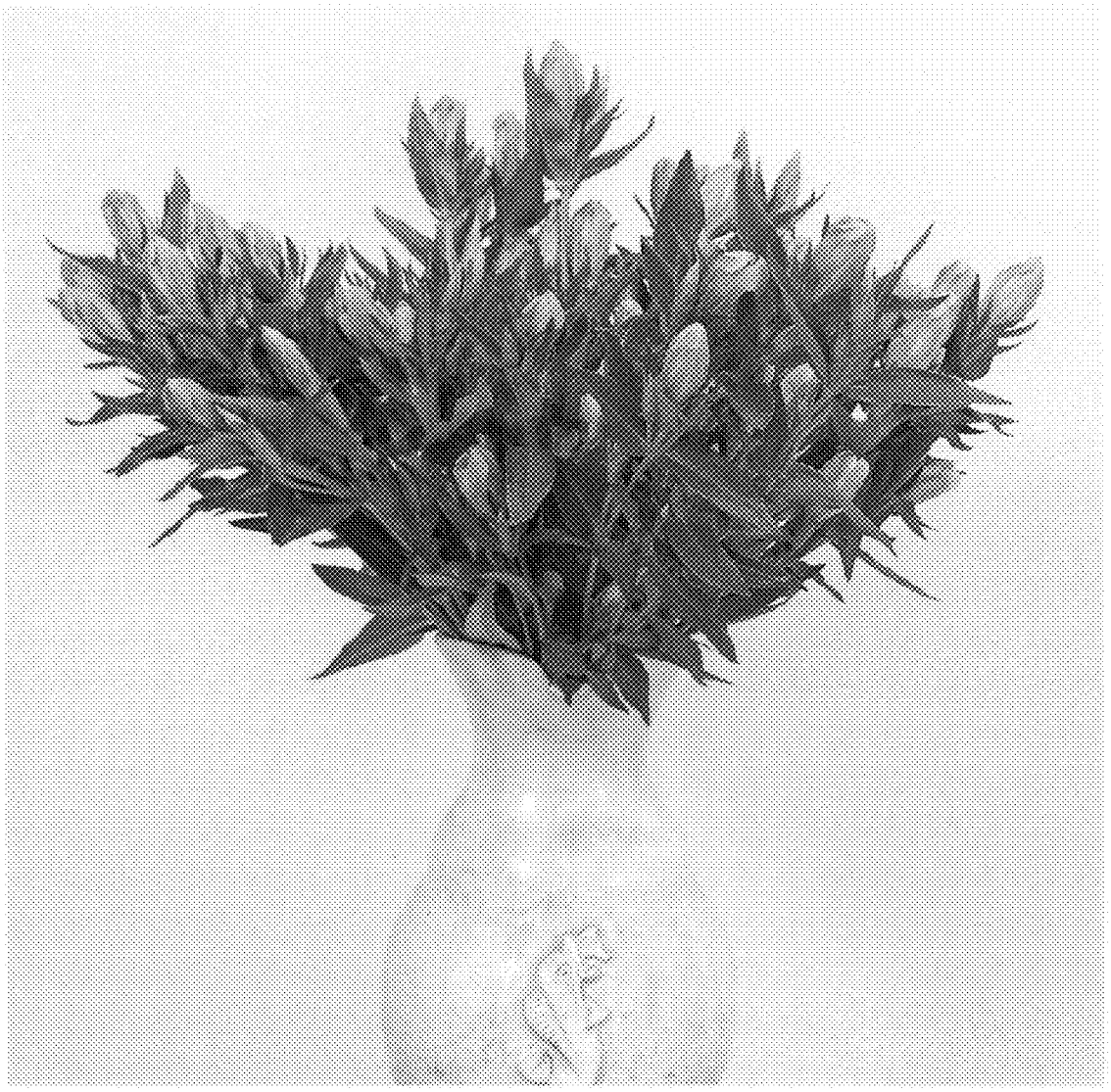

The photograph in FIG. 1 provides a view of cut stems of 'Blue Magic'.

Figure 2:
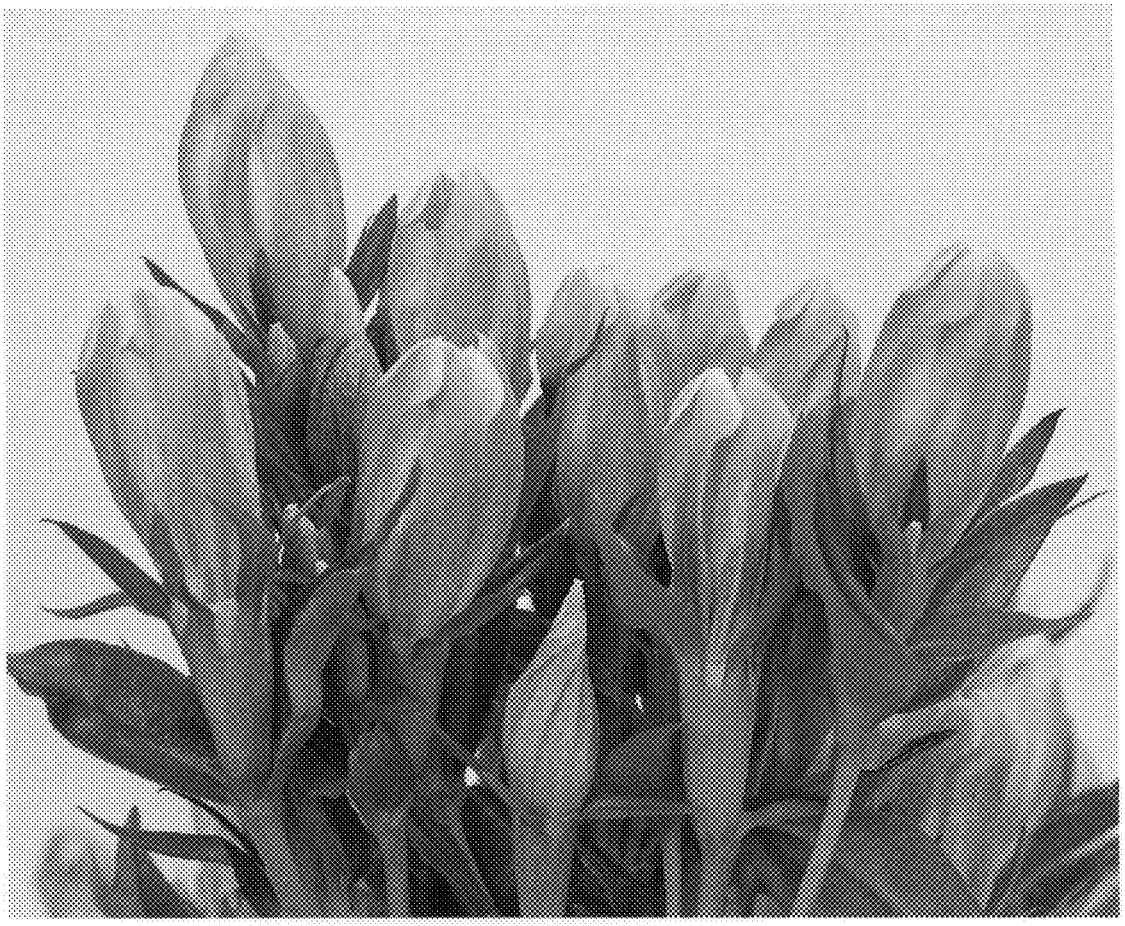

The photograph in FIG. 2 provides a close-up view of flowers of 'Blue Magic'.

Figure 3:
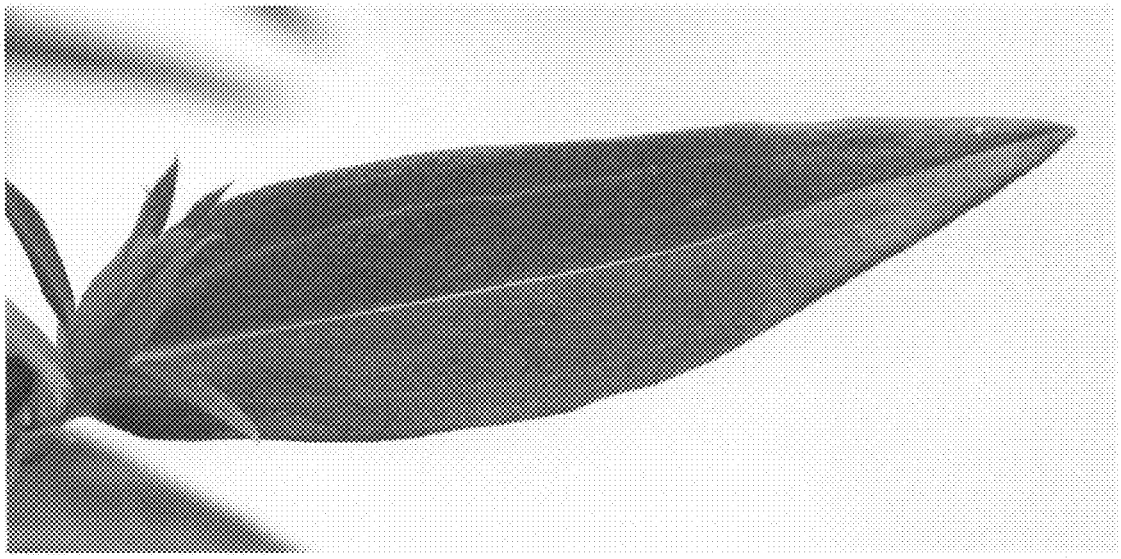

The photograph in FIG. 3 provides a close-up view of a leaf of 'Blue Magic'.

The colors in the photograph may differ slightly from the color values cited in the detailed botanical description, which accurately describe the colors of the new Gentian.

DETAILED BOTANICAL DESCRIPTION

The following is a detailed description of two year-old plants the new cultivar as grown in a field in Reeuwijk, The Netherlands under natural light with average day temperatures ranging from 14° to 32° C. and average night temperatures ranging from 6° to 18° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—Continuously from mid June to mid July in The Netherlands.

*Plant type.*—Herbaceous perennial.

*Plant habit.*—Clump-forming, narrowly upright, compact, uniform.

*Height and spread.*—Average of 72 cm in height and 69 cm in spread.

*Cold hardiness.*—At least to U.S.D.A. Zone 6.

*Heat tolerance.*—At least to 35° C.

*Diseases and pests.*—Not more susceptible than other cultivars of *Gentiana makinoi.*

*Root description.*—Fine.

Growth and propagation:

*Propagation.*—Stem cuttings and tissue culture.

*Root initiation.*—Roots appear on cuttings in about 10 days when grown at about 25° C. in a greenhouse without supplemental lighting during the summer months.

*Root development.*—Roots fully develop in a 13 cm pots in about 3 months from a rooted cutting.

*Cropping time to bloom.*—About 3 months from a cutting or rooted transplant from tissue culture.

*Growth rate.*—Moderately vigorous, growing about 20 cm per month in the spring.

Stem description:

*Stem shape.*—Round.

*Stem color.*—144B.

*Stem size.*—Lateral branches; an average of 14.2 cm in length (range of 4.2 to 27 cm), average of 2 mm in diameter.

*Stem surface.*—Slightly glossy, smooth.

*Stem aspect.*—Upright, strong.

*Internode length.*—Average of 4.6 cm.

*Branching habit.*—Basal branching, about 12 un-branched stems emerge from each main stem.

*No. of harvestable cut flower stems.*—10 per year.

Foliage description:

*Leaf shape.*—Lanceolate to narrowly elliptic.

*Leaf division.*—Simple.

*Leaf base.*—Cuneate.

*Leaf apex.*—Acute.

*Leaf venation.*—Pinnate, only midrib is conspicuous, color on upper surface is 143C, color on lower surface is 144B to 144C.

*Leaf margins.*—Entire.

*Leaf attachment.*—Sessile.

*Leaf arrangement.*—Opposite.

*Leaf surface.*—Dull, slightly leathery and glabrous on upper and lower surface.

*Leaf color.*—Young upper surface; color between 141A and 143A, young lower surface; color between 144B and 146C, mature upper surface; 137A, mature lower surface; 144A to 144B.

*Leaf number.*—An average of 6 per lateral branch with a range from 2 to 10 depending on branch length.

*Leaf size.*—Average of 6.6 cm in length and 1.9 cm in width.

*Leaf substance.*—Moderate durability to environmental stresses.

Flower description:

*Flower type.*—Axillary and terminal tubular flowers, arising singularly or in pairs or clusters of 3.

*Flower fragrance.*—Moderate, cinnamon-like scent.

*Flower lastingness.*—Average of 10 days on plant and 14 days as a cut flower, persistent.

*Flower bud description.*—Narrowly elliptic in shape, average of 6 mm in diameter and 2.9 cm in length, color 144C with immature calyx portion 143B to 143C.

*Flower quantity.*—Average of 5 per lateral stem, an average of 50 per two year-old plant.

*Flower aspect.*—Upright.

*Flower shape.*—Tubular with base fused and upper 15% free.

*Flower size.*—4.7 cm in depth and 1.7 cm in diameter.

*Rate of opening.*—About 50% fully open at flowering peak.

*Peduncles.*—Average of 0.8 cm in length and 2 mm in diameter, held upright, 144C in color, strong, occur on axillary flowers with terminal flowers sessile to stem.

*Pedicels.*—None.

*Petals.*—5, about 4.5 cm in length and 8 mm in width, oblong in shape, 85% of lower portion is fused into a tubular shape, margin is entire, apex is broadly acute, surface is smooth and slightly glossy in appearance, color (opening and fully open); outer surface 96D to 97A dotted with 144A to 144B and base 145A, inner surface (opening and fully open); outer surface 96D dotted with 144A to 144B and base 145A, fading of both surfaces; 79D.

*Calyx form.*—Campanulate in form, average of 1.8 cm in length and 1.4 cm in diameter.

*Sepals.*—5, average of 1.8 cm in length, 2 mm in width, base fused with free tips linear to lanceolate in shape, margin is entire, apex is narrowly acute, base is fused, surface is smooth and dull in appearance, color of inner surface is 141A to 141B, color of outer surface is 143B to 143C.

Reproductive organs:

*Gynoecium.*—1 pistil, about 3.3 cm in length, stigma is linear and decurrent when ovary develops and 149D in color, style is about 3 cm in length 145B in color, ovary is 144B to 144C in color.

*Androecium.*—5 stamens, anthers are oblong in shape, basifixed, about 3 mm in length and 4C in color, filaments are about 2.2 cm in length and 155C in color on upper portion and 145B in color on lower portion, pollen is low in quantity and 4B in color.

*Seed.*—No seed production has been observed under the conditions tested.

It is claimed:

1. A new and distinct cultivar of *Gentiana makinoi* plant named 'Blue Magic' as herein illustrated and described.

* * * * *